United States Patent [19]

Labovitz et al.

[11] 4,014,942
[45] Mar. 29, 1977

[54] NOVEL ACETAL
[75] Inventors: Jeffery N. Labovitz; Clive A. Henrick, both of Palo Alto, Calif.
[73] Assignee: Zoecon Corporation, Palo Alto, Calif.
[22] Filed: Mar. 29, 1976
[21] Appl. No.: 671,911

Related U.S. Application Data

[62] Division of Ser. No. 602,153, Aug. 6, 1975.
[52] U.S. Cl. .................. 260/615 A; 260/632 Y; 260/642 R; 260/405; 260/405.5; 260/410; 260/488 H; 424/312; 424/314
[51] Int. Cl.² .......................................... C07C 43/30

[58] Field of Search ................................ 260/615 A

[56] References Cited
UNITED STATES PATENTS 3,919,329  11/1975  Anderson et al. ............. 260/615 A Primary Examiner—Howard T. Mars
Attorney, Agent, or Firm—Donald W. Erickson

[57] ABSTRACT

Synthesis of, and intermediates for, trans-4, cis-7 tridecadienyl acetate, attractant for the male potato tuberworm moth.

1 Claim, No Drawings

NOVEL ACETAL

This is a division of application Ser. No. 602,153, filed Aug. 6, 1975.

This invention relates to the synthesis of, and intermediates for, the compound trans-4, cis-7 tridecadienyl acetate which is an attractant for the male potato tuberworm moth.

The potato tuberworm moth, *Phthorimaea operculella* is a pest of potatoes in many areas of the world. The synthesis of the male attractant, tridecadienyl acetate, with the isomeric requirement trans(E) at C-4 and cis(Z) at C-7 is of considerable utility. The synthetic compound is useful for monitoring the insect population and thereby determine the need for applying insecticide.

The synthesis of the present invention can be outlined as follows:

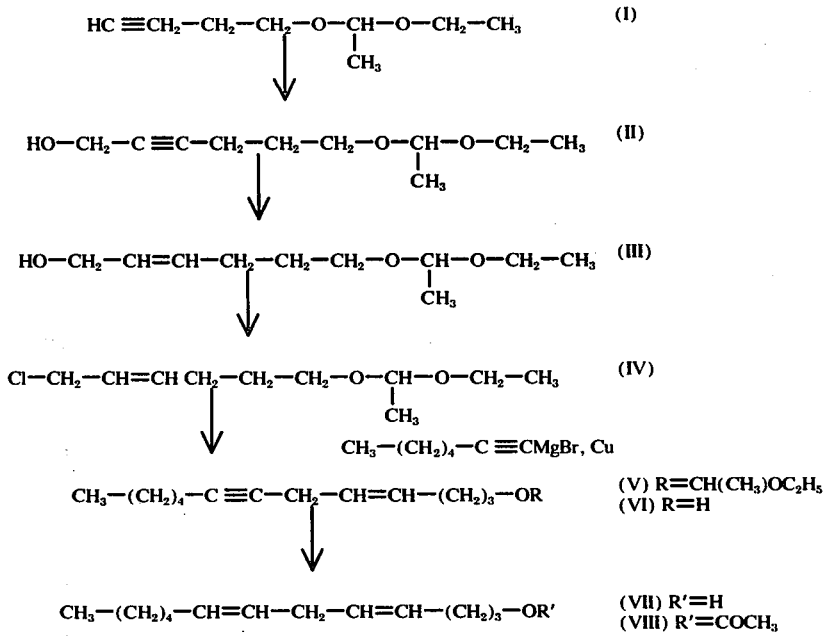

In the practice of the above outlined synthesis, the acetal T is prepared by the reaction of ethyl vinyl ether and 4-pentyn-1-ol in the presence of p-toluenesulfonic acid. CF. Eaton et al, J. Org. Chem. 37, 1947 (1972). The acetal I is then treated with n-butyllithium to prepare the lithium salt thereof which is reacted with paraformaldehyde to obtain the acetylenic alcohol II. Stereoselective reduction of the acetylenic alcohol II with lithium aluminum hydride in tetrahydrofuran under reflux gives the trans allylic alcohol III. The alcohol III is then converted to the allylic chloride IV using methanesulfonyl chloride, lithium chloride, and 2,4,6-trimethylpyridine without any detectable rearrangement or loss of stereochemistry and without attack on the acid-sensitive acetal protecting group. CF. Collington et al, J. Org. Chem. 36, 3044 (1971). The allylic chloride IV is then reacted with 1-heptynyl-1-magnesium bromide by heating in tetrahydrofuran under reflux in the presence of a catalytic quantity of cuprous chloride to yield the 4E-ene-7-yne acetal V. Hydrolysis of the acetal VI with trichloroacetic acid gives the alcohol VI which is crystallized from pentane at -74° and then distilled to give pure 4E-ene-7-yne alcohol VI.

Careful partial hydrogenation of the alcohol VI at 0° over Lindlar catalyst in hexane containing synthetic quinoline gives 4E,7Z-dienyl alcohol VII which is acetylated to yield 4E,7Z-tridecadien-1-yl acetate VIII (98% purity by glc analysis).

The attractant VIII is used in conjunction with an insect trap which is provided with a sticky surface to hold the adult moth. A charge of about 100 to 500 micrograms of VIII in a suitable inert holder such as a small polyethylene cap or a rubber septa is a sufficient amount to lure the adult male moth to the trap. The cap or septa is held in place by the sticky surface of the cap. The attractant can also be mixed with a resin or wax and extruded or molded at low temperature to produce large quantities of the attractant in convenient form for use. A suitable polymeric carrier is described by McKibben et al., U.S. Pat. No. 3,803,303.

The following examples are provided to illustrate the practice of the present invention. Temperature is given in degrees Centigrade.

EXAMPLE 1

To 72 g (1mol) of ethyl vinyl ether was added 70 mg (0.37 mmol) of p-toluenesulfonic acid monohydrate and the solution was cooled to 0°. 4-Pentyn-1-ol (44 g; 0.52 mol) was then added at ≤ 20° and the reaction was stirred at ≤ 20° for 1 hr. The reaction was then cooled to 0° and 5 ml of saturated aqueous $K_2CO_3$ was added. After 15 min., solid $K_2CO_3$ was added to remove the water and the solution was filtered and the excess ethyl vinyl ether was removed from the filtrate at atmospheric pressure. The residue was distilled in vacuo to give 66.79 g (82% yield) of the acetal I, bp 70°–72° (20 mm) nmr ($CCl_4$) δ 1.16 (t, 3, $\underline{J}$ = 7Hz, $OCH_2C\underline{H}_3$), 1.23 [$d$, 3, $\underline{J}$ = 5.5 Hz, $OCH(C\underline{H}_3)O$], 1.76 (m, 3, $OC\underline{H}_2CH_3$ and C ≡ CH), 2.28 ($m$, 2, $C\underline{H}_2C$ ≡ CH), and 4.62 ppm [$q$, 1, $\underline{J}$ = 5.5 Hz, $OC\underline{H}$ ($CH_3$)O].

EXAMPLE 2

To 70 ml of ether cooled to −10° was added 64.6 ml (0.10 mol) of 1.55 M n-butyl-lithium in hexane and then 15.6 g (0.10 mol) of the acetal I was added while maintaining the temperature at ≤ −10°. The solution was then stirred for 10 min and then 30 ml of tetrahydrofuran was added at −10°. The solution was warmed to 0° and 3.60 g (0.12 mol) of paraformaldehyde was added in one portion. The reaction was allowed to warm to room temperature over 45 min and then was heated under reflux for 3 hr. The solution was then cooled to room temperature and poured into ice water and the mixture was extracted with ether:pentane (1:1). The organic layer was washed with saturated aqueous NH$_4$Cl and was dried (MgSO$_4$). Removal of the solvent in vacuo followed by distillation of the residue gave 13.24 g (71% yield) of the acetylenic alcohol II, bp 91° (0.20 mm) nmr (CCl$_4$) δ 1.17 (t, 3, J = 7 Hz, OCH$_2$CH$_3$), 1.23 [d, 3, J = 5.5 Hz, OCH(CH$_3$)O], 3.05 (t, 1, J = 5.5 Hz, OH), 4.10 (m, 2, CH$_2$OH), and 4.62 ppm [q, 1, J = 5.5 Hz, OCH(CH$_3$)O].

Anal. Calcd for C$_{10}$H$_{18}$O$_3$. C, 64.49; H, 9.74. Found: C, 64.29; H, 9.73.

EXAMPLE 3

To 12.24 g (65.7 mmol) of the acetylenic alcohol II in 120 ml of tetrahydrofuran was added 15.8 (68 mmol) of 4.3 M lithium aluminum hydride in ether and the reaction mixture was heated under reflux for 1.5 hr. The solution was then cooled, and ice was added to destroy the excess reagent and the reaction mixture was poured into saturated aqueous NH$_4$Cl. The mixture was extracted with ether:hexane (1:1) and the organic layers were combined and washed with saturated aqueous NH$_4$Cl, brine and were dried (MgSO$_4$). Removal of the solvent and distillation of the residue gave 10.44 g (84.4% yield) of the alcohol III, (98% pure by glc analysis), bp 102°–104° (0.40 mm) nmr (CCl$_4$) δ 1.17 (t, 3, J = 7 Hz, OCH$_2$CH$_3$), 1.23 [d, 3, J = 5.5 Hz, OCH(CH$_3$)O], 3.97 (br s, 2, CH$_2$OH), 4.62 [q, 1, J = 5.5 Hz, OCH(CH$_3$)O], and 5.62 ppm (m, 2, CH=CH).

Anal. Calcd for C$_{10}$H$_{20}$O$_3$: C, 63.80; H, 10.71. Found: C, 63.82; H, 10.60.

EXAMPLE 4

To 13.8 g (0.114 mol) of 2,4,6-trimethylpyridine and 19.58 g (0.104 mol) of the alcohol III was added 4.41 g (0.104 mol) of lithium chloride dissolved in 80 ml of dimethylformamide. The mixture was cooled to 0° and 13 g (0.114 mol) of methanesulfonyl chloride was added. The yellow solution was stirred for 3.5 hr at 3° and then was poured into ice-water and the mixture was extracted with pentane. The pentane layer was washed with aqueous CuSO$_4$, brine, and was dried (Na$_2$SO$_4$) and the solvent was removed to give 20 g (93% yield) of the allylic chloride IV: nmr (CCl$_4$) δ 1.14 (t, 3, J = 7 Hz, OCH$_2$CH$_3$), 1.21 [d, 3, J = 5.5 Hz, OCH(CH$_3$)O], 3.96 (d, 2, J = 6 Hz, CH$_2$Cl), 4.57 [q, 1, J = 5.5 Hz, OCH(CH$_3$)O], and 5.67 ppm (m, 2, CH=CH).

EXAMPLE 5

To a solution of 1-heptynyl-1-magnesium bromide (prepared from 120 mmol of 1-heptyne and 120 mmol of EtMgBr in 120 ml of tetrahydrofuran, heated under reflux for 2 hr) was added 1.60 g (16 mmol) of cuprous chloride and the mixture stirred at room temperature for 20 min. Then 20 g (0.097 mol) of the allylic chloride IV in 30 ml of tetrahydrofuran was added and the reaction mixture was stirred to 60° for 4.5 hr. After the mixture had been cooled, aqueous NH$_4$Cl was added and the mixture was extracted with pentane. The pentane layer was washed with saturated aqueous NH$_4$Cl, brine, and dried (MgSO$_4$) and the solvent was removed to give 25.12 g (97% yield) of crude acetal V, bp 103°–104° (0.12 mm) nmr (CCl$_4$) δ 1.13 (t, 3, J = 7 Hz, OCH$_2$CH$_3$), 1.21 [d, 3, J = 5.5 Hz, OCH(CH$_3$)O], 2.75 (br s, 2, C≡CCH$_2$CH=CH), 4.54 [q, 1, J = 5.5 Hz, OCH(CH$_3$)O], and 5.47 ppm (m, 2, CH=CH).

EXAMPLE 6

To a solution of 25.12 g (94.3 mmol) of the acetal V in 250 ml of tetrahydrofuran was added 50 ml of water and 0.5 g (3.06 mmol) of trichloroacetic acid and the mixture was stirred at room temperature for 17 hr, and then was heated under reflux for 5 hr. To the cooled solution was added 25 ml of 2 M aqueous Na$_2$CO$_3$ and the mixture was extracted with ether. The organic layer was washed with saturated aqueous NaCl and was dried (MgSO$_4$), and the solvent was removed and the residue was distilled to give 12.63 g (69% yield) of the alcohol VI. The distilled material was crystallized by dissolving it in 120 ml of pentane and cooling the solution to −74° and collecting the crystals at −74° to yield 11.04 g (60% yield) of VI (98.8% pure by glc analysis): bp 95° (0.10 mm) nmr (CCl4) δ 2.78 (br s, 1, C≡CCH$_2$CH=CH), 3.58 (t, 2, J = 6 Hz, CH$_2$OH), and 5.52 ppm (m, 2, HC=CH).

Anal. Calcd for C$_{13}$H$_{22}$O: C, 80.35, H, 11.41. Found: C, 80.19; H, 11.43.

EXAMPLE 7

A solution of 11.04 g (57 mmol) of the alcohol VI in 40 ml tetrahydrofuran was added to a prehydrogenated suspension of 1.36 g of Lindlar Catalyst (from Engelhard Industries) in 150 ml of hexane containing 0.33 ml of synthetic quinoline at 0°. The acetylene was hydrogenated at 2°–4° (the reaction was followed by glc). When the reaction was complete (by glc analysis) celite was added and the mixture was filtered, and the solvent was removed from the filtrate. Distillation of the residue gave 9.53 g (85% yield) of the diene VII: bp 83°–85° (0.09 mm) nmr (CCl$_4$) δ 2.70 (br s, CH=CHCH$_2$CH=CH), 3.55 (t, 2, J = 6 Hz, CH$_2$OH), and 5.40 ppm (m, 4, CH=CHCH$_2$CH=CH).

Anal. Calcd for C$_{13}$H$_{24}$O: C, 79.53; H, 12.32. Found: C, 79.56; H, 12.25.

EXAMPLE 8

To a solution of 9.13 g (46.5 mmol) of the diene VII in 9.37 ml (0.116 mol) of pyridine was added 5.50 ml (58.3 mmol) of acetic anhydride. The solution was stirred 23 hr at room temperature, then was cooled to 0°, and ice was added, and the solution was poured into ice and water and the mixture was extracted with pentane. The pentane layer was washed with ice cold aqueous 10% HCl, and 5% aqueous NaHCO$_3$, brine was dried (Na$_2$SO$_4$). The solution was filtered through a column of 80 g of florisil (Act. III), using pentane as eluent. Removal of the pentane from the eluate followed by distillation of the residue gave 8.30 g (74.9% yield) of VIII (97.7% pure by glc analysis at 180° on a 4 m × 2 mm (i.d.) glass column packed with 10% OV-17 on 100/120 mesh Chromosorb W-AW-DMCS), bp 75°–80° (0.03 mm) nmr (CCl$_4$) δ 1.99 (s, 3, COCH$_3$), 2.71 (br s, 2, CH=CHCH$_2$CH=CH), 3.99 (t, 2, J = 6 Hz, CH$_2$OAc), and 5.38 ppm (m, 4, CH=CHCH$_2$CH=CH); mass spectrum (20 ev) m/e (rel intensity) M$^+$ 238 (~0), 178 (22), 150 (14), 135 (16), 121 (33), 107 (38), 93 (74), and 79 (100).

Anal. Calcd for $C_{15}H_{26}O_2$: C, 75.58; H, 11.00. Found: C, 75.75; H, 10.89.
Nmr spectra were determined on a Varian T-60 spectrometer. Gas-liquid chromatographic analysis (glc) were performed on Model 402 Hewlett-Packard instruments equipped with hydrogen flame ionization detectors.
What is claimed is:
1. The trans compound of the formula:
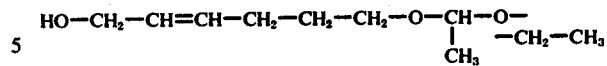
* * * * *

UNITED STATES PATENT OFFICE
CERTIFICATE OF CORRECTION

Patent No. 4,014,942    Dated March 29, 1977

Inventor(s) JEFFERY N. LABOVITZ; CLIVE A. HENRICK

It is certified that error appears in the above-identified patent and that said Letters Patent are hereby corrected as shown below:

In column, that part of formula (I) which reads "$HC\equiv CH_2-CH_2-$" should read -- $HC\equiv C-CH_2-CH_2-$ --.

Signed and Sealed this

Twenty-seventh Day of September 1977

[SEAL]

Attest:

RUTH C. MASON
Attesting Officer

LUTRELLE F. PARKER
Acting Commissioner of Patents and Trademarks